（12) United States Patent
Dishler et al.

(10) Patent No.: US 8,057,541 B2
(45) Date of Patent: Nov. 15, 2011

(54) METHOD OF USING SMALL DIAMETER INTRACORNEAL INLAYS TO TREAT VISUAL IMPAIRMENT

(75) Inventors: Jon Dishler, Cherry Hills Village, CO (US); Troy A. Miller, Rancho Santa Margarita, CA (US); Alexander Vatz, Lake Forest, CA (US); James R. Alexander, Newport Beach, CA (US)

(73) Assignee: ReVision Optics, Inc., Lake Forest, CA (US)

( * ) Notice: Subject to any disclaimer, the term of this patent is extended or adjusted under 35 U.S.C. 154(b) by 801 days.

(21) Appl. No.: 11/554,544

(22) Filed: Oct. 30, 2006

(65) Prior Publication Data

US 2007/0203577 A1    Aug. 30, 2007

Related U.S. Application Data

(60) Provisional application No. 60/776,458, filed on Feb. 24, 2006.

(51) Int. Cl.
*A61F 2/14* (2006.01)
*A61F 2/16* (2006.01)

(52) U.S. Cl. ........................... 623/5.11; 623/6.11
(58) Field of Classification Search ............. 623/5.11
See application file for complete search history.

(56) References Cited

U.S. PATENT DOCUMENTS

| 2,714,721 | A | 8/1955 | Stone, Jr. |
| 3,168,100 | A | 2/1965 | Rich |
| 3,343,657 | A | 9/1967 | Speshyock |
| 3,379,200 | A | 4/1968 | Pennell |
| 3,482,906 | A | 12/1969 | Volk |
| 3,743,337 | A | 7/1973 | Crary |
| 3,770,113 | A | 11/1973 | Thomas |
| 3,879,076 | A | 4/1975 | Barnett |
| 3,950,315 | A | 4/1976 | Cleaver |
| 3,996,627 | A | 12/1976 | Deeg et al. |

(Continued)

FOREIGN PATENT DOCUMENTS

DE    3208729 A1    9/1983

(Continued)

OTHER PUBLICATIONS

Dishler, Jon et al.; U.S. Appl. No. 11/692,835 entitled "Insertion system for corneal implants," filed Mar. 28, 2007.

(Continued)

*Primary Examiner* — Thomas J Sweet
*Assistant Examiner* — Jacqueline Woznicki
(74) *Attorney, Agent, or Firm* — Shay Glenn LLP

(57) ABSTRACT

Provided herein are small diameter inlays for correcting vision impairments by altering the shape of the anterior corneal surface. In an embodiment, inlays having diameters smaller than the pupil are provided for correcting presbyopia. To provide near vision, an inlay is implanted centrally in the cornea to induce an "effective" zone on the anterior corneal surface, within which diopter power is increased. Distance vision is provided by a region of the cornea peripheral to the "effect" zone. In another embodiment, small diameter inlays are provided that induce effective optical zones on the anterior corneal surface that are much larger in diameter than the inlays. The increase in the effective optical zone, due at least in part to a draping effect, allows an inlay to produce a much larger clinical effect on a patient's vision than the diameter of the inlay.

38 Claims, 7 Drawing Sheets

U.S. PATENT DOCUMENTS

| | | | |
|---|---|---|---|
| 4,030,480 A | 6/1977 | Meyer | |
| 4,037,604 A | 7/1977 | Newkirk | |
| 4,039,827 A | 8/1977 | Zdrok et al. | |
| 4,065,816 A | 1/1978 | Sawyer | |
| 4,071,272 A | 1/1978 | Drdlik | |
| 4,136,406 A | 1/1979 | Norris | |
| 4,157,718 A | 6/1979 | Baehr | |
| 4,184,491 A | 1/1980 | McGannon | |
| 4,194,814 A | 3/1980 | Fischer et al. | |
| 4,238,524 A | 12/1980 | LaLiberte et al. | |
| 4,257,521 A | 3/1981 | Poler | |
| 4,268,133 A | 5/1981 | Fischer et al. | |
| 4,326,306 A | 4/1982 | Poler | |
| 4,357,940 A | 11/1982 | Muller | |
| 4,392,569 A | 7/1983 | Shoup | |
| 4,418,991 A | 12/1983 | Breger | |
| 4,423,809 A | 1/1984 | Mazzocco | |
| 4,428,746 A | 1/1984 | Mendez | |
| 4,452,235 A | 6/1984 | Reynolds | |
| 4,466,705 A | 8/1984 | Michelson | |
| 4,490,860 A | 1/1985 | Rainin | |
| 4,504,982 A | 3/1985 | Burk | |
| 4,521,210 A | 6/1985 | Wong | |
| 4,525,044 A | 6/1985 | Bauman | |
| 4,545,478 A | 10/1985 | Waldman | |
| 4,554,115 A | 11/1985 | Neefe | |
| 4,554,918 A | 11/1985 | White | |
| 4,565,198 A | 1/1986 | Koeniger | |
| 4,580,882 A | 4/1986 | Nuchman et al. | |
| 4,586,929 A | 5/1986 | Binder | |
| 4,604,087 A | 8/1986 | Joseph | |
| 4,607,617 A | 8/1986 | Choyce | |
| 4,616,910 A | 10/1986 | Klein | |
| 4,618,227 A | 10/1986 | Bayshore | |
| 4,619,256 A | 10/1986 | Horn | |
| 4,624,664 A | 11/1986 | Peluso et al. | |
| 4,624,669 A | 11/1986 | Grendahl | |
| 4,640,595 A | 2/1987 | Volk | |
| 4,646,720 A | 3/1987 | Peyman et al. | |
| 4,655,774 A | 4/1987 | Choyce | |
| 4,662,370 A | 5/1987 | Hoffmann et al. | |
| 4,663,358 A | 5/1987 | Hyon et al. | |
| 4,671,276 A | 6/1987 | Reynolds | |
| 4,676,792 A | 6/1987 | Praeger | |
| 4,697,697 A | 10/1987 | Graham et al. | |
| 4,702,244 A | 10/1987 | Mazzocco | |
| 4,709,697 A | 12/1987 | Muller | |
| 4,726,367 A | 2/1988 | Shoemaker | |
| 4,750,901 A | 6/1988 | Molteno | |
| 4,762,496 A | 8/1988 | Maloney et al. | |
| 4,766,895 A | 8/1988 | Reynolds | |
| 4,769,033 A | 9/1988 | Nordan | |
| 4,772,283 A | 9/1988 | White | |
| 4,778,462 A | 10/1988 | Grendahl | |
| 4,798,609 A | 1/1989 | Grendahl | |
| 4,806,382 A | 2/1989 | Goldberg et al. | |
| 4,836,201 A | 6/1989 | Patton et al. | |
| 4,840,175 A * | 6/1989 | Peyman | 606/5 |
| 4,842,599 A | 6/1989 | Bronstein | |
| 4,844,242 A | 7/1989 | Chen et al. | |
| 4,851,003 A | 7/1989 | Lindstrom | |
| 4,860,885 A | 8/1989 | Kaufman et al. | |
| 4,886,488 A | 12/1989 | White | |
| 4,888,016 A | 12/1989 | Langerman | |
| 4,897,981 A | 2/1990 | Beck | |
| 4,911,715 A | 3/1990 | Kelman | |
| 4,919,130 A | 4/1990 | Stoy et al. | |
| 4,923,467 A | 5/1990 | Thompson | |
| 4,934,363 A | 6/1990 | Smith et al. | |
| 4,936,825 A | 6/1990 | Ungerleider | |
| 4,946,436 A | 8/1990 | Smith | |
| 4,955,903 A | 9/1990 | Sulc et al. | |
| 4,968,296 A | 11/1990 | Ritch et al. | |
| 4,971,732 A | 11/1990 | Wichterle | |
| 4,976,719 A | 12/1990 | Siepser | |
| 5,019,084 A | 5/1991 | Aysta et al. | |
| 5,019,098 A | 5/1991 | Mercier | |
| 5,022,414 A | 6/1991 | Muller | |
| 5,030,230 A | 7/1991 | White | |
| 5,041,081 A | 8/1991 | Odrich | |
| 5,063,942 A | 11/1991 | Kilmer et al. | |
| 5,071,276 A | 12/1991 | Nielsen et al. | |
| 5,073,163 A | 12/1991 | Lippman | |
| 5,092,837 A | 3/1992 | Ritch et al. | |
| 5,098,444 A | 3/1992 | Feaster | |
| 5,108,428 A | 4/1992 | Capecchi et al. | |
| 5,112,350 A | 5/1992 | Civerchia et al. | |
| 5,123,905 A | 6/1992 | Kelman | |
| 5,123,921 A | 6/1992 | Werblin et al. | |
| 5,139,518 A | 8/1992 | White | |
| 5,171,213 A | 12/1992 | Price, Jr. | |
| 5,173,723 A | 12/1992 | Volk | |
| 5,178,604 A | 1/1993 | Baerveldt et al. | |
| 5,180,362 A | 1/1993 | Worst | |
| 5,181,053 A | 1/1993 | Brown | |
| 5,188,125 A | 2/1993 | Kilmer et al. | |
| 5,190,552 A | 3/1993 | Kelman | |
| 5,192,317 A | 3/1993 | Kalb | |
| 5,196,026 A | 3/1993 | Barrett et al. | |
| 5,211,660 A | 5/1993 | Grasso | |
| 5,225,858 A | 7/1993 | Portney | |
| 5,229,797 A | 7/1993 | Futhey et al. | |
| 5,244,799 A | 9/1993 | Anderson | |
| 5,258,042 A | 11/1993 | Mehta | |
| 5,270,744 A | 12/1993 | Portney | |
| 5,273,750 A | 12/1993 | Homiger et al. | |
| 5,282,851 A | 2/1994 | Jacob-LaBarre | |
| 5,300,020 A | 4/1994 | L'Esperance, Jr. | |
| 5,300,116 A | 4/1994 | Chirila et al. | |
| 5,312,413 A | 5/1994 | Eaton et al. | |
| 5,318,044 A | 6/1994 | Kilmer et al. | |
| 5,318,046 A | 6/1994 | Rozakis | |
| 5,318,047 A | 6/1994 | Davenport et al. | |
| 5,336,261 A * | 8/1994 | Barrett et al. | 623/5.11 |
| 5,338,291 A | 8/1994 | Speckman et al. | |
| 5,344,448 A | 9/1994 | Schneider et al. | |
| 5,346,464 A | 9/1994 | Camras | |
| 5,370,607 A | 12/1994 | Memmen | |
| 5,372,577 A | 12/1994 | Ungerleider | |
| 5,385,582 A | 1/1995 | Ommaya | |
| 5,391,201 A | 2/1995 | Barrett et al. | |
| 5,397,300 A | 3/1995 | Baerveldt et al. | |
| 5,405,384 A | 4/1995 | Silvestrini | |
| 5,428,412 A | 6/1995 | Stoyan | |
| 5,433,701 A | 7/1995 | Rubinstein | |
| 5,454,796 A | 10/1995 | Krupin | |
| 5,458,819 A | 10/1995 | Chirila et al. | |
| 5,467,149 A | 11/1995 | Morrison et al. | |
| 5,474,562 A | 12/1995 | Orchowski et al. | |
| 5,476,445 A | 12/1995 | Baerveldt et al. | |
| 5,489,301 A | 2/1996 | Barber | |
| 5,493,350 A | 2/1996 | Seidner | |
| 5,502,518 A | 3/1996 | Lieberman | |
| 5,512,220 A | 4/1996 | Roffman et al. | |
| 5,520,631 A | 5/1996 | Nordquist et al. | |
| 5,521,656 A | 5/1996 | Portney | |
| 5,530,491 A | 6/1996 | Baude et al. | |
| 5,533,997 A * | 7/1996 | Ruiz | 606/5 |
| 5,570,142 A | 10/1996 | Lieberman | |
| 5,591,185 A | 1/1997 | Kilmer et al. | |
| 5,598,234 A | 1/1997 | Blum et al. | |
| 5,616,148 A | 4/1997 | Eagles et al. | |
| 5,620,450 A | 4/1997 | Eagles et al. | |
| 5,628,794 A | 5/1997 | Lindstrom | |
| 5,630,810 A | 5/1997 | Machat | |
| 5,634,943 A | 6/1997 | Villain et al. | |
| 5,643,276 A | 7/1997 | Zaleski | |
| 5,657,108 A | 8/1997 | Portney | |
| 5,682,223 A | 10/1997 | Menezes et al. | |
| 5,684,560 A | 11/1997 | Roffman et al. | |
| 5,715,031 A | 2/1998 | Roffman et al. | |
| 5,716,633 A | 2/1998 | Civerchia | |
| 5,722,948 A | 3/1998 | Gross | |
| 5,722,971 A * | 3/1998 | Peyman | 606/5 |
| 5,728,155 A | 3/1998 | Anello et al. | |
| 5,752,928 A | 5/1998 | de Roulhac et al. | |
| 5,755,785 A | 5/1998 | Rowsey et al. | |

| Patent | Kind | Date | Inventor |
|---|---|---|---|
| 5,766,181 | A | 6/1998 | Chambers et al. |
| 5,772,667 | A | 6/1998 | Blake |
| 5,785,674 | A | 7/1998 | Mateen |
| 5,800,442 | A | 9/1998 | Wolf et al. |
| 5,800,529 | A | 9/1998 | Brauker et al. |
| 5,805,260 | A | 9/1998 | Roffman et al. |
| 5,810,833 | A | 9/1998 | Brady et al. |
| 5,817,115 | A | 10/1998 | Nigam |
| 5,824,086 | A | 10/1998 | Silvestrini |
| 5,847,802 | A | 12/1998 | Menezes et al. |
| 5,855,604 | A | 1/1999 | Lee |
| 5,860,984 | A | 1/1999 | Chambers et al. |
| 5,872,613 | A | 2/1999 | Blum et al. |
| 5,873,889 | A | 2/1999 | Chin |
| 5,876,439 | A | 3/1999 | Lee |
| 5,888,243 | A | 3/1999 | Silverstrini |
| 5,913,898 | A | 6/1999 | Feingold |
| 5,919,185 | A | 7/1999 | Peyman |
| 5,928,245 | A | 7/1999 | Wolf et al. |
| 5,929,968 | A | 7/1999 | Cotie et al. |
| 5,929,969 | A | 7/1999 | Roffman |
| 5,941,583 | A | 8/1999 | Raimondi |
| 5,944,752 | A | 8/1999 | Silvestrini |
| 5,945,498 | A | 8/1999 | Hopken et al. |
| 5,964,748 | A | 10/1999 | Peyman |
| 5,964,776 | A | 10/1999 | Peyman |
| 5,968,065 | A | 10/1999 | Chin |
| 5,976,150 | A | 11/1999 | Copeland |
| 5,976,168 | A | 11/1999 | Chin |
| 5,980,549 | A | 11/1999 | Chin |
| 6,007,510 | A | 12/1999 | Nigam |
| 6,010,510 | A | 1/2000 | Brown et al. |
| 6,024,448 | A | 2/2000 | Wu et al. |
| 6,033,395 | A | 3/2000 | Peyman |
| 6,036,714 | A | 3/2000 | Chin |
| 6,050,999 | A | 4/2000 | Paraschac et al. |
| 6,055,990 | A | 5/2000 | Thompson |
| 6,066,170 | A | 5/2000 | Lee |
| 6,068,642 | A | 5/2000 | Johnson et al. |
| 6,079,826 | A | 6/2000 | Appleton et al. |
| 6,083,231 | A | 7/2000 | Van Noy et al. |
| 6,086,202 | A | 7/2000 | Chateau et al. |
| 6,090,141 | A | 7/2000 | Lindstrom |
| 6,102,946 | A | 8/2000 | Nigam |
| 6,110,166 | A | 8/2000 | Juhasz et al. |
| 6,120,148 | A | 9/2000 | Fiala et al. |
| 6,125,294 | A | 9/2000 | Scholl et al. |
| 6,129,733 | A | 10/2000 | Brady et al. |
| 6,139,560 | A | 10/2000 | Kremer |
| 6,142,969 | A | 11/2000 | Nigam |
| 6,143,001 | A | 11/2000 | Brown et al. |
| 6,159,241 | A | 12/2000 | Lee et al. |
| 6,171,324 | B1 | 1/2001 | Cote et al. |
| 6,175,754 | B1 | 1/2001 | Scholl et al. |
| RE37,071 | E | 2/2001 | Gabrielian et al. |
| 6,183,513 | B1 | 2/2001 | Guenthner et al. |
| 6,197,019 | B1 | 3/2001 | Peyman |
| 6,197,057 | B1 | 3/2001 | Peyman et al. |
| 6,197,058 | B1 | 3/2001 | Portney |
| 6,203,538 | B1 | 3/2001 | Peyman |
| 6,203,549 | B1 | 3/2001 | Waldock |
| 6,203,557 | B1 | 3/2001 | Chin |
| 6,206,919 | B1 | 3/2001 | Lee |
| 6,210,005 | B1 | 4/2001 | Portney |
| 6,214,015 | B1 | 4/2001 | Reich et al. |
| 6,214,044 | B1 | 4/2001 | Silverstrini |
| 6,217,571 | B1 | 4/2001 | Peyman |
| 6,221,067 | B1 | 4/2001 | Peyman |
| 6,228,114 | B1 | 5/2001 | Lee |
| 6,248,111 | B1 | 6/2001 | Glick et al. |
| 6,250,757 | B1 | 6/2001 | Roffman et al. |
| 6,251,114 | B1 | 6/2001 | Farmer et al. |
| 6,264,648 | B1 | 7/2001 | Peyman |
| 6,264,670 | B1 | 7/2001 | Chin |
| 6,264,692 | B1 | 7/2001 | Woffinden et al. |
| 6,267,768 | B1 | 7/2001 | Deacon et al. |
| 6,271,281 | B1 | 8/2001 | Liao et al. |
| 6,277,137 | B1 | 8/2001 | Chin |
| 6,280,449 | B1 | 8/2001 | Blake |
| 6,280,470 | B1 | 8/2001 | Peyman |
| 6,283,595 | B1 | 9/2001 | Breger |
| 6,302,877 | B1* | 10/2001 | Ruiz ................................ 606/5 |
| 6,325,509 | B1 | 12/2001 | Hodur et al. |
| 6,325,792 | B1 | 12/2001 | Swinger et al. |
| 6,361,560 | B1* | 3/2002 | Nigam ........................ 623/5.14 |
| 6,364,483 | B1 | 4/2002 | Grossinger et al. |
| 6,371,960 | B2 | 4/2002 | Heyman et al. |
| 6,391,230 | B1 | 5/2002 | Sarbadhikari |
| 6,398,277 | B1 | 6/2002 | McDonald |
| 6,398,789 | B1 | 6/2002 | Capetan |
| 6,428,572 | B2 | 8/2002 | Nagai |
| 6,435,681 | B2 | 8/2002 | Portney |
| 6,436,092 | B1 | 8/2002 | Peyman |
| 6,447,519 | B1 | 9/2002 | Brady et al. |
| 6,447,520 | B1 | 9/2002 | Ott et al. |
| 6,458,141 | B1 | 10/2002 | Peyman |
| 6,461,384 | B1 | 10/2002 | Hoffmann et al. |
| 6,471,708 | B2 | 10/2002 | Green |
| 6,474,814 | B1 | 11/2002 | Griffin |
| 6,506,200 | B1 | 1/2003 | Chin |
| 6,511,178 | B1 | 1/2003 | Roffman et al. |
| 6,527,389 | B2 | 3/2003 | Portney |
| 6,537,283 | B2 | 3/2003 | Van Noy |
| 6,543,610 | B1 | 4/2003 | Nigam |
| 6,544,286 | B1 | 4/2003 | Perez |
| 6,551,307 | B2 | 4/2003 | Peyman |
| 6,554,424 | B1 | 4/2003 | Miller et al. |
| 6,554,425 | B1 | 4/2003 | Roffman et al. |
| 6,557,998 | B2 | 5/2003 | Portney |
| 6,581,993 | B2 | 6/2003 | Nigam |
| 6,582,076 | B1 | 6/2003 | Roffman et al. |
| 6,589,203 | B1 | 7/2003 | Mitrev |
| 6,589,280 | B1 | 7/2003 | Koziol |
| 6,592,591 | B2 | 7/2003 | Polla et al. |
| 6,596,000 | B2 | 7/2003 | Chan et al. |
| 6,605,093 | B1 | 8/2003 | Blake |
| 6,607,537 | B1 | 8/2003 | Binder |
| 6,607,556 | B1 | 8/2003 | Nigam |
| 6,623,522 | B2 | 9/2003 | Nigam |
| 6,626,941 | B2 | 9/2003 | Nigam |
| 6,629,979 | B1 | 10/2003 | Feingold et al. |
| 6,632,244 | B1 | 10/2003 | Nigam |
| 6,645,246 | B1 | 11/2003 | Weinschenk, III et al. |
| 6,648,877 | B1 | 11/2003 | Juhasz et al. |
| 6,657,029 | B2 | 12/2003 | Vanderbilt |
| 6,666,887 | B1 | 12/2003 | Callahan et al. |
| 6,673,112 | B2 | 1/2004 | Nigam |
| 6,709,103 | B1 | 3/2004 | Roffman et al. |
| 6,712,848 | B1 | 3/2004 | Wolf et al. |
| 6,723,104 | B2 | 4/2004 | Ott |
| 6,733,507 | B2 | 5/2004 | McNicholas et al. |
| 6,733,526 | B2 | 5/2004 | Paul et al. |
| 6,808,262 | B2 | 10/2004 | Chapoy et al. |
| 6,824,178 | B2 | 11/2004 | Nigam |
| 6,855,163 | B2 | 2/2005 | Peyman |
| 6,875,232 | B2 | 4/2005 | Nigam |
| 6,879,402 | B2 | 4/2005 | Küchel |
| 6,881,197 | B1 | 4/2005 | Nigam |
| 6,893,461 | B2 | 5/2005 | Nigam |
| 6,949,093 | B1 | 9/2005 | Peyman |
| 7,128,351 | B2 | 10/2006 | Nigam |
| 2001/0027314 | A1* | 10/2001 | Peyman ............................ 606/5 |
| 2001/0051826 | A1 | 12/2001 | Bogaert et al. |
| 2002/0055753 | A1 | 5/2002 | Silvestrini |
| 2002/0101563 | A1 | 8/2002 | Miyamura et al. |
| 2002/0103538 | A1 | 8/2002 | Hughes et al. |
| 2003/0014042 | A1 | 1/2003 | Juhasz et al. |
| 2003/0033010 | A1 | 2/2003 | Hicks et al. |
| 2003/0069637 | A1 | 4/2003 | Lynch et al. |
| 2003/0078487 | A1 | 4/2003 | Jeffries et al. |
| 2003/0229303 | A1 | 12/2003 | Haffner et al. |
| 2004/0019379 | A1 | 1/2004 | Glick et al. |
| 2004/0034413 | A1 | 2/2004 | Christensen |
| 2004/0049267 | A1 | 3/2004 | Nigam |
| 2004/0054408 | A1 | 3/2004 | Glick et al. |
| 2004/0073303 | A1 | 4/2004 | Schanzlin |
| 2005/0080484 | A1 | 4/2005 | Marmo et al. |
| 2005/0080485 | A1 | 4/2005 | Nigam |

| | | |
|---|---|---|
| 2005/0113844 A1 | 5/2005 | Nigam |
| 2005/0119738 A1 | 6/2005 | Nigam |
| 2005/0143717 A1 | 6/2005 | Peyman |
| 2005/0178394 A1 | 8/2005 | Slade |
| 2005/0182350 A1 | 8/2005 | Nigam |
| 2005/0203494 A1 | 9/2005 | Holliday |
| 2005/0246015 A1 | 11/2005 | Miller |
| 2005/0246016 A1 | 11/2005 | Miller et al. |
| 2006/0020267 A1 | 1/2006 | Marmo |
| 2006/0116762 A1 | 6/2006 | Hong et al. |
| 2006/0142780 A1 | 6/2006 | Pynson et al. |
| 2006/0142781 A1 | 6/2006 | Pynson et al. |
| 2006/0212041 A1 | 9/2006 | Nigam |
| 2006/0235430 A1 | 10/2006 | Le et al. |
| 2007/0027538 A1 | 2/2007 | Aharoni et al. |
| 2007/0129797 A1 | 6/2007 | Lang et al. |
| 2007/0255401 A1 | 11/2007 | Lang |
| 2007/0280994 A1 | 12/2007 | Cunanan |
| 2008/0262610 A1* | 10/2008 | Lang et al. ............ 623/5.16 |
| 2009/0198325 A1* | 8/2009 | Holliday et al. ......... 623/5.11 |

FOREIGN PATENT DOCUMENTS

| | | |
|---|---|---|
| EP | 0308077 A2 | 3/1989 |
| EP | 0420549 A2 | 4/1991 |
| JP | 01-195853 | 8/1989 |
| JP | 02-211119 | 8/1990 |
| JP | 5502811 | 5/1993 |
| JP | 08-501009 | 2/1996 |
| JP | 9-504706 | 5/1997 |
| JP | 2000506056 | 5/2000 |
| JP | 03-508135 | 3/2003 |
| WO | WO 96/26690 A1 | 9/1996 |
| WO | WO 98/08549 A1 | 3/1998 |
| WO | WO 98/48715 A1 | 11/1998 |
| WO | WO 99/17691 A1 | 4/1999 |
| WO | WO 99/21513 A1 | 5/1999 |
| WO | WO 99/30645 A2 | 6/1999 |
| WO | WO 00/38594 A1 | 7/2000 |
| WO | WO 03/041616 A1 | 5/2003 |
| WO | WO 03/061518 A2 | 7/2003 |
| WO | WO 03/101341 A2 | 12/2003 |
| WO | WO 2006/029316 A1 | 4/2006 |
| WO | WO 2006/060363 A2 | 6/2006 |
| WO | WO 2007/101016 A2 | 9/2007 |

OTHER PUBLICATIONS

Lang, Alan et al.; U.S. Appl. No. 11/738,349 entitled "Biomechanical design of intracorneal inlays," filed Apr. 20, 2007.

Churms, P.W., The Theory and Computation of Optical Modifications to the Cornea in Refractive Keratoplasty, American Journal of Optometry & Physiological Optics, 56:2, pp. 67-74, Feb. 1979.

Alio, J. J., et al., Intracorneal Inlay Complicated by Intrastomal Epithelial Opacification, Arch Ophthalmol, vol. 122, Oct. 2004.

Warsky, M.A. et al., "Predicting Refractive Alterations with Hydrogel Keratophakia," Investigative Opthalmology & Visual Science, vol. 26, pp. 240-243, Feb. 1985.

Liou, H. L. et al., "Anatomically accurate, finite model eye for optical modeling", Journal of the Optical Society of America, vol. 14, No. 8, Aug. 1997.

Cheng, et al.; "Predicting subjective judgment of best focus with objective image quality metrics"; Journal of Vision; vol. 4, pp. 310-321, 2004.

Marsack, et al.; "Metrics of optical quality derived from wave aberrations predict visual performance"; Journal of Vision; vol. 4; pp. 322-328; 2004.

Holliday et al.; U.S. Appl. No. 12/418,325 entitled "Corneal Inlay Design and Methods of Correcting Vision," filed Apr. 3, 2009.

Huang et al.; Mathematical Model of Corneal Surface Smoothing After Laser Refractive Surgery; American Journal of Ophthalmology; Mar. 2003; pp. 267-278.

Navarro et al.; Accommodation-dependent model of the human eye with aspherics; J. Opt. Soc Am. A; vol. 2; No. 8; Aug. 1985; pp. 1273-1281.

Dishler et al.; U.S. Appl. No. 12/861,656 entitled "Methods and Devices for Forming Corneal Channels," filed Aug. 23, 2010.

* cited by examiner

METHOD OF USING SMALL DIAMETER INTRACORNEAL INLAYS TO TREAT VISUAL IMPAIRMENT

RELATED APPLICATION

This application claims the benefit of U.S. Provisional Application Ser. No. 60/776,458, filed on Feb. 24, 2006.

FIELD OF THE INVENTION

The field of the invention relates generally to corneal implants, and more particularly, to intracorneal inlays.

BACKGROUND INFORMATION

As is well known, abnormalities in the human eye can lead to vision impairment. Some typical abnormalities include variations in the shape of the eye, which can lead to myopia (near-sightedness), hyperopia (far-sightedness) and astigmatism as well as variations in the tissue present throughout the eye, such as a reduction in the elasticity of the lens, which can lead to presbyopia. A variety of technologies have been developed to try and address these abnormalities, including corneal implants.

Corneal implants can correct vision impairment by altering the shape of the cornea. Corneal implants can be classified as an onlay or an inlay. An onlay is an implant that is placed over the cornea such that the outer layer of the cornea, e.g., the epithelium, can grow over and encompass the implant. An inlay is an implant that is surgically implanted into the cornea beneath a portion of the corneal tissue by, for example, cutting a flap in the cornea and inserting the inlay beneath the flap. Both inlays and outlays can alter the refractive power of the cornea by changing the shape of the anterior cornea, by having a different index of refraction than the cornea, or both. Since the cornea is the strongest refracting optical element in the human ocular system, altering the cornea's anterior surface is a particularly useful method for correcting vision impairments caused by refractive errors. Inlays are also useful for correcting other visual impairments including presbyopia.

SUMMARY

Provided herein are small diameter inlays for correcting vision impairments by altering the shape of the anterior corneal surface.

In one embodiment, inlays having diameters smaller than the diameter of the pupil are provided for correcting presbyopia. To provide near vision, an inlay is implanted centrally in the cornea to induce an "effect" zone on the anterior corneal surface that is smaller than the optical zone of the cornea, wherein the "effect" zone is the area of the anterior corneal surface affected by the inlay. The implanted inlay increases the curvature of the anterior corneal surface within the "effect" zone, thereby increasing the diopter power of the cornea within the "effect" zone. Because the inlay is smaller than the diameter of the pupil, light rays from distance objects by-pass the inlay and refract using the region of the cornea peripheral to the "effect" zone to create an image of the distant objects on the retina.

The small diameter inlays may be used alone or in conjunction with other refractive procedures. In an embodiment, a small diameter inlay is used in conjunction with LASIK for correcting myopia or hyperopia. In this embodiment, a LASIK procedure is used to correct for distance refractive error and the small diameter inlay is used to provide near vision for presbyopic subjects.

In another embodiment, small diameter inlays are provided that induce effective optical zones on the anterior corneal surface that are much larger in diameter than the inlays. The increase in the effective optical zone allows an inlay to produce a much larger clinical effect on a patient's vision than the diameter of the inlay.

In one embodiment, the effective optical zone induced by the inlay is increased by increasing the draping effect of the inlay. The draping effect extends the area of the anterior corneal surface affected by the inlay, and thereby the effective optical zone induced by the inlay. In an embodiment, the draping effect is increased by increasing the finite edge thickness of the inlay for a given inlay diameter and center thickness.

In another embodiment, inlays having effective optical zones much larger than the inlay diameter are used to correct hyperopia. In this embodiment, the draping effect extends the area of the anterior corneal surface where the curvature is increased, thereby extending the effective optical zone of the inlay and providing increased diopter power over a wider diameter than the inlay diameter. This increase in the effective optical zone allows for the correction of hyperopia using smaller diameter inlays.

Other systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims. It is also intended that the invention not be limited to the details of the example embodiments.

DETAILED DESCRIPTION

Figure 1:
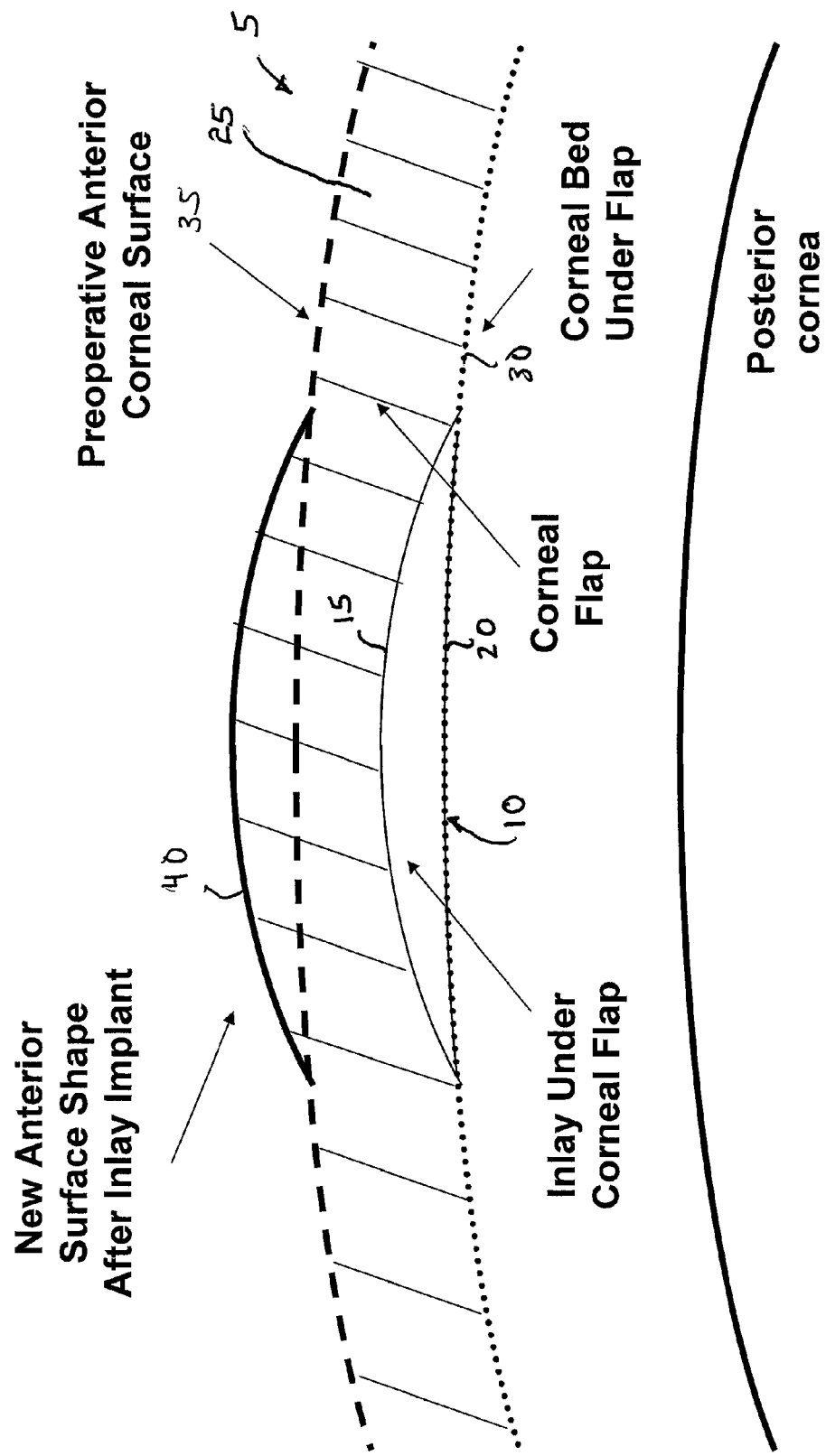
FIG. 1 is a cross-sectional view of a cornea showing an intracorneal inlay implanted in the cornea according to an embodiment of the invention.

FIG. 1 shows an example of an intracorneal inlay 10 implanted in a cornea 5. The inlay 10 may have a meniscus shape with an anterior surface 15 and a posterior surface 20. The inlay 10 is preferably implanted in the cornea at a depth of 50% or less of the cornea (approximately 250 µm or less), and is placed on the stromal bed 30 of the cornea created by a micro keratome. The inlay 10 may be implanted in the cornea 5 by cutting a flap 25 into the cornea, lifting the flap 25 to expose the cornea's interior, placing the inlay 10 on the exposed area of the cornea's interior, and repositioning the flap 25 over the inlay 10. The flap 25 may be cut using a laser, e.g., a femtosecond laser, a mechanical keratome or manually by an ophthalmic surgeon. When the flap 25 is cut into the cornea, a small section of corneal tissue is left intact to create a hinge for the flap 25 so that the flap 25 can be repositioned accurately over the inlay 20. After the flap 25 is repositioned over the inlay, the cornea heals around the flap 25 and seals the flap 25 back to the un-cut peripheral portion of the anterior corneal surface. Alternatively, a pocket or well having side walls or barrier structures may be cut into the cornea, and the inlay inserted between the side walls or barrier structures through a small opening or "port" in the cornea.

The inlay 10 changes the refractive power of the cornea by altering the shape of the anterior corneal surface. In FIG. 1, the pre-operative anterior corneal surface is represented by dashed line 35 and the post-operative anterior corneal surface induced by the underlying inlay 10 is represented by solid line 40.

The inlay may have properties similar to those of the cornea (e.g., index of refraction around 1.376, water content of 78%, etc.), and may be made of hydrogel or other clear bio-compatible material. To increase the optical power of the inlay, the inlay may be made of a material with a higher index of refraction than the cornea, e.g., >1.376. Materials that can be used for the inlay include, but are not limited to, Lidofilcon A, Poly-HEMA, poly sulfone, silicone hydrogel, and the like. The index of refraction may be in the range of 1.33 to 1.55.

Presbyopic Inlays

This section discusses the use of small intracorneal inlays having diameters that are small in comparison with the pupil for correcting presbyopia. In the preferred embodiment, a small inlay (e.g., 1 to 2 mm in diameter) is implanted centrally in the cornea to induce an "effect" zone on the anterior corneal surface that is smaller than the optical zone of the cornea for providing near vision. Here, "effect" zone is the area of the anterior corneal surface affected by the inlay. The implanted inlay increases the curvature of the anterior corneal surface within the "effect" zone, thereby increasing the diopter power of the cornea within the "effect" zone. Distance vision is provided by the region of the cornea peripheral to the "effect" zone.

Presbyopia is characterized by a decrease in the ability of the eye to increase its power to focus on nearby objects due to a loss of elasticity in the crystalline lens with age. Typically, a person suffering from Presbyopia requires reading glasses to provide near vision.

Figure 2:
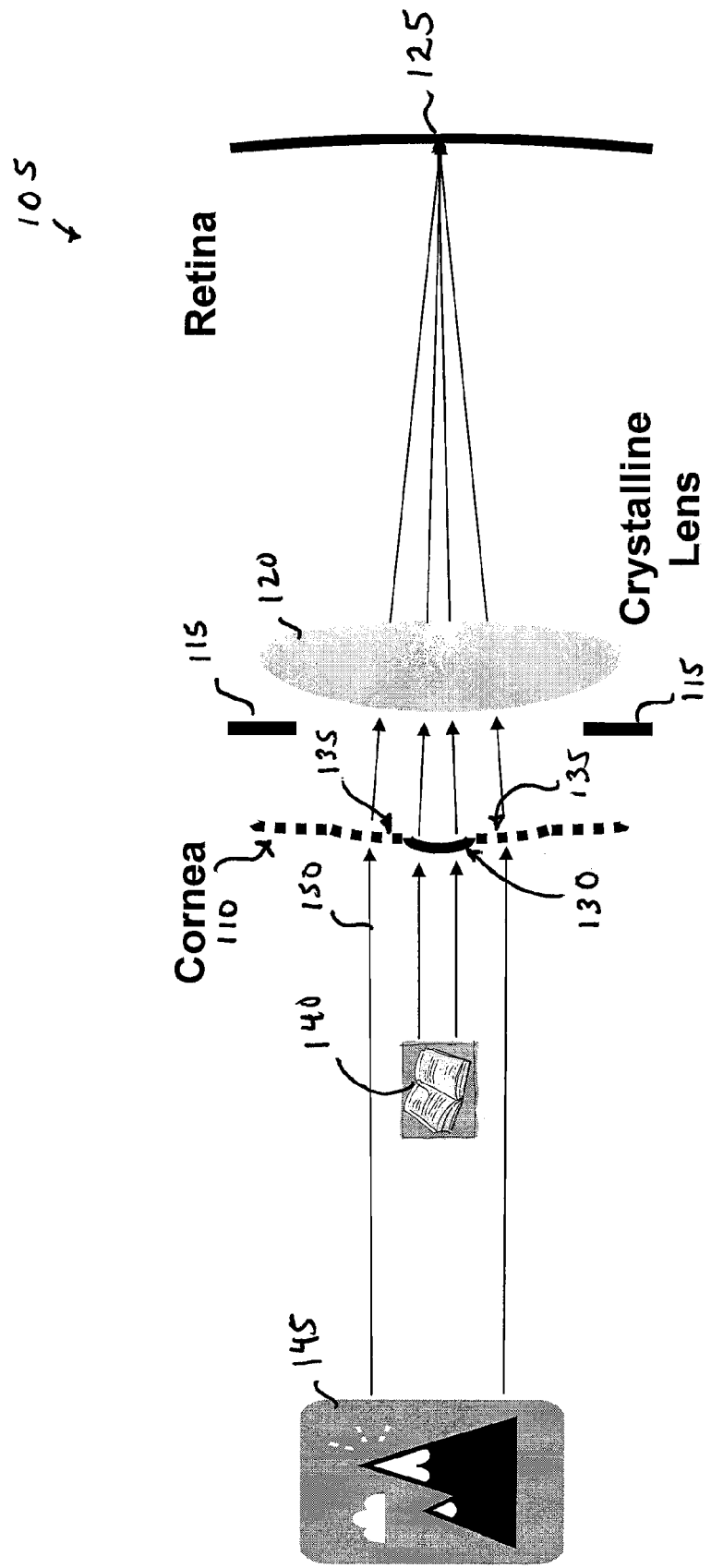
FIG. 2 is a diagram of an eye illustrating the use of a small diameter inlay to provide near vision according to an embodiment of the invention.

FIG. 2 shows an example of how a small inlay can provide near vision to a subject's eye while retaining some distance vision according to an embodiment of the invention. The eye 105 comprises the cornea 110, the pupil 115, the crystalline lens 120 and the retina 125. In this example, the small inlay (not shown) is implanted centrally in the cornea to create a small diameter "effect" zone 130. The small inlay has a smaller diameter than the pupil 115 so that the resulting "effect" zone 130 has a smaller diameter than the optical zone of the cornea. The "effect" zone 130 provides near vision by increasing the curvature of the anterior corneal surface, and therefore the diopter power within the "effect" zone 130. The region 135 of the cornea peripheral to the "effect" zone provides distance vision.

To increase the diopter power within the "effect" zone 130, the small inlay has a higher curvature than the pre-implant anterior corneal surface to increase the curvature of the anterior corneal surface within the "effect" zone 130. The inlay may further increase the diopter power within the "effect" zone 130 by having an index of refraction that is higher than the index of refraction of the cornea ($n_{cornea}$=1.376). Thus, the increase in the diopter power within the "effect" zone 130 may be due to the change in the anterior corneal surface induced by the inlay or a combination of the change in the anterior cornea surface and the index of refraction of the inlay. For early presbyopes (e.g., about 45 to 55 years of age), at least 1 diopter is typically required for near vision. For complete presbyopes (e.g., about 60 years of age or older), between 2 and 3 diopters of additional power is required.

An advantage of the small intracorneal inlay is that when concentrating on nearby objects 140, the pupil naturally becomes smaller (e.g., near point miosis) making the inlay effect even more effective. Further increases in the inlay effect can be achieved by simply increasing the illumination of a nearby object (e.g., turning up a reading light).

Because the inlay is smaller than the diameter of the pupil 115, light rays 150 from distant objects 145 by-pass the inlay and refract using the region of the cornea peripheral to the "effect" zone to create an image of the distant objects on the retina 125, as shown in FIG. 2. This is particularly true with larger pupils. At night, when distance vision is most important, the pupil naturally becomes larger, thereby reducing the inlay effect and maximizing distance vision.

A subject's natural distance vision is in focus only if the subject is emmetropic (i.e., does not require glasses for distance vision). Many subjects are ammetropic, requiring either myopic or hyperopic refractive correction. Especially for myopes, distance vision correction can be provided by myopic Laser in Situ Keratomileusis (LASIK), Laser Epithelial Keratomileusis (LASEK), Photorefractive Keratectomy (PRK) or other similar corneal refractive procedures. After the distance corrective procedure is completed, the small inlay can be implanted in the cornea to provide near vision. Since LASIK requires the creation of a flap, the inlay may be inserted concurrently with the LASIK procedure. The inlay may also be inserted into the cornea after the LASIK procedure since the flap can be re-opened. Therefore, the small inlay may be used in conjunction with other refractive procedures, such as LASIK for correcting myopia or hyperopia.

Figure 3:
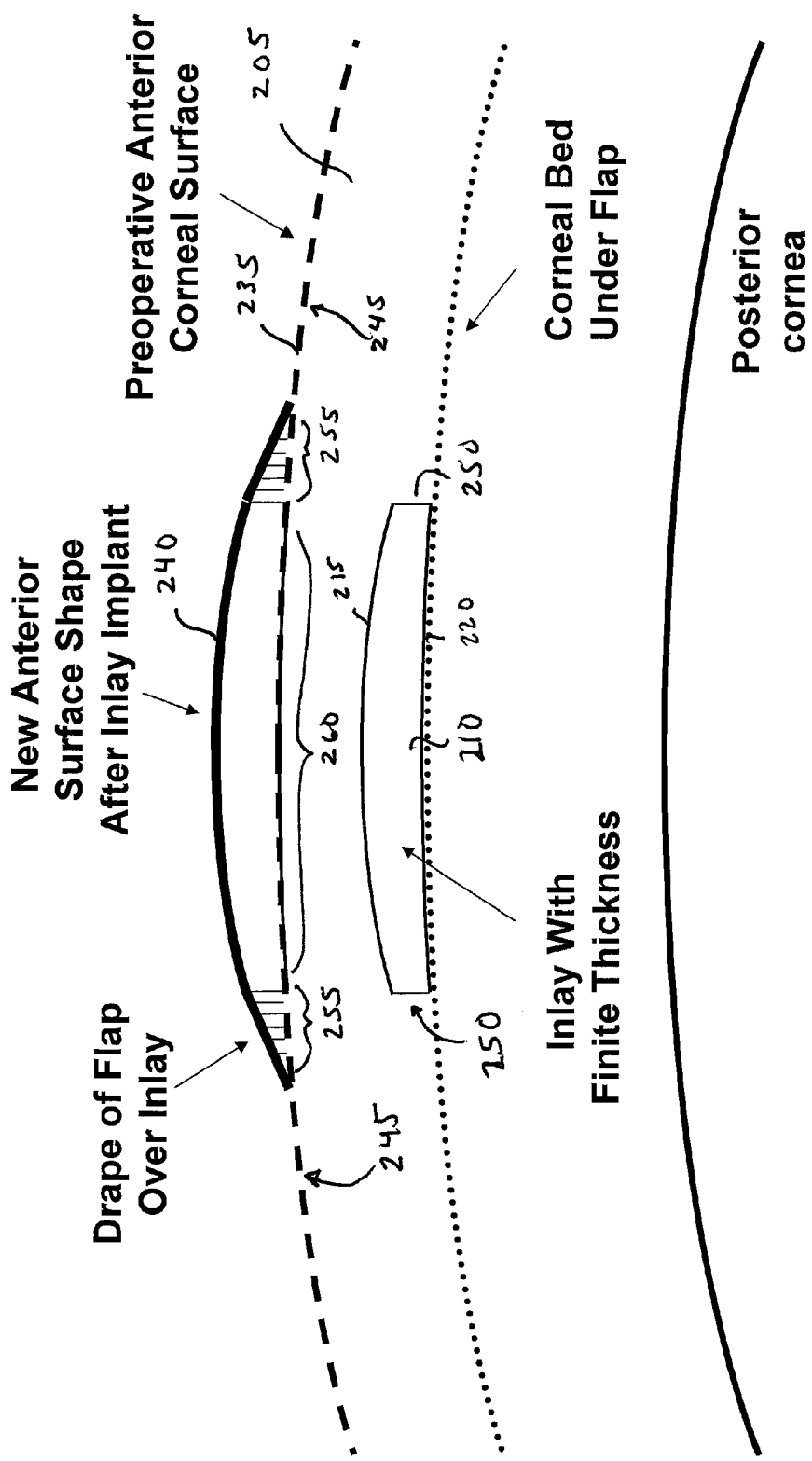
FIG. 3 is a cross-sectional view of a cornea showing an inlay implanted in the cornea and a change in the anterior corneal surface induced by the inlay including a drape region according to an embodiment of the invention.

A method for designing a small inlay to provide near vision will now be described. FIG. 3 shows a small inlay 210 implanted in the cornea 205 and the change in the shape of the anterior corneal surface 240 induced by the inlay 210. In FIG. 3, the pre-implant anterior corneal surface is represented by dashed line 235 and the post-implant anterior corneal surface induced by the inlay 210 is represented by solid line 240. The inlay 210 does not substantially affect the shape of the anterior corneal surface in the region of the cornea 210 peripheral to the "effect" zone so that distance vision is undisturbed in the peripheral 245. In the case where a distance corrective procedure is performed prior to implantation of the inlay, the pre-implant anterior corneal surface 235 is the anterior corneal surface after the distance corrective procedure but before implantation of the inlay.

The inlay 210 has a finite edge thickness 250. The edge thickness 250 can not be made zero due to the finite material properties of the inlay. The finite edge thickness 250 of the inlay produces a draping effect, as described further below. To minimize the draping effect, the edge thickness 250 of the inlay 210 can be made as small as possible, e.g., less than about 20 microns. In addition to a finite edge thickness 250, the inlay may have a tapered region (not shown) that tapers downward from the anterior surface 215 of the inlay to the edge 250 of the inlay. The tapered region may be 10-30 μm in length.

In FIG. 3, the portion of the anterior corneal surface directly above the inlay is altered by the physical shape of the inlay 210. Because of the finite edge thickness 250 of the inlay 210, the anterior corneal surface does not immediately return to its pre-implant shape for a diameter larger than the physical inlay 210. Eventually, the anterior corneal surface returns to the pre-implant corneal surface 235. Therefore, the draping effect produces a drape region 255 that extends the shape change of the anterior corneal surface induced by the inlay 210.

Figure 4:
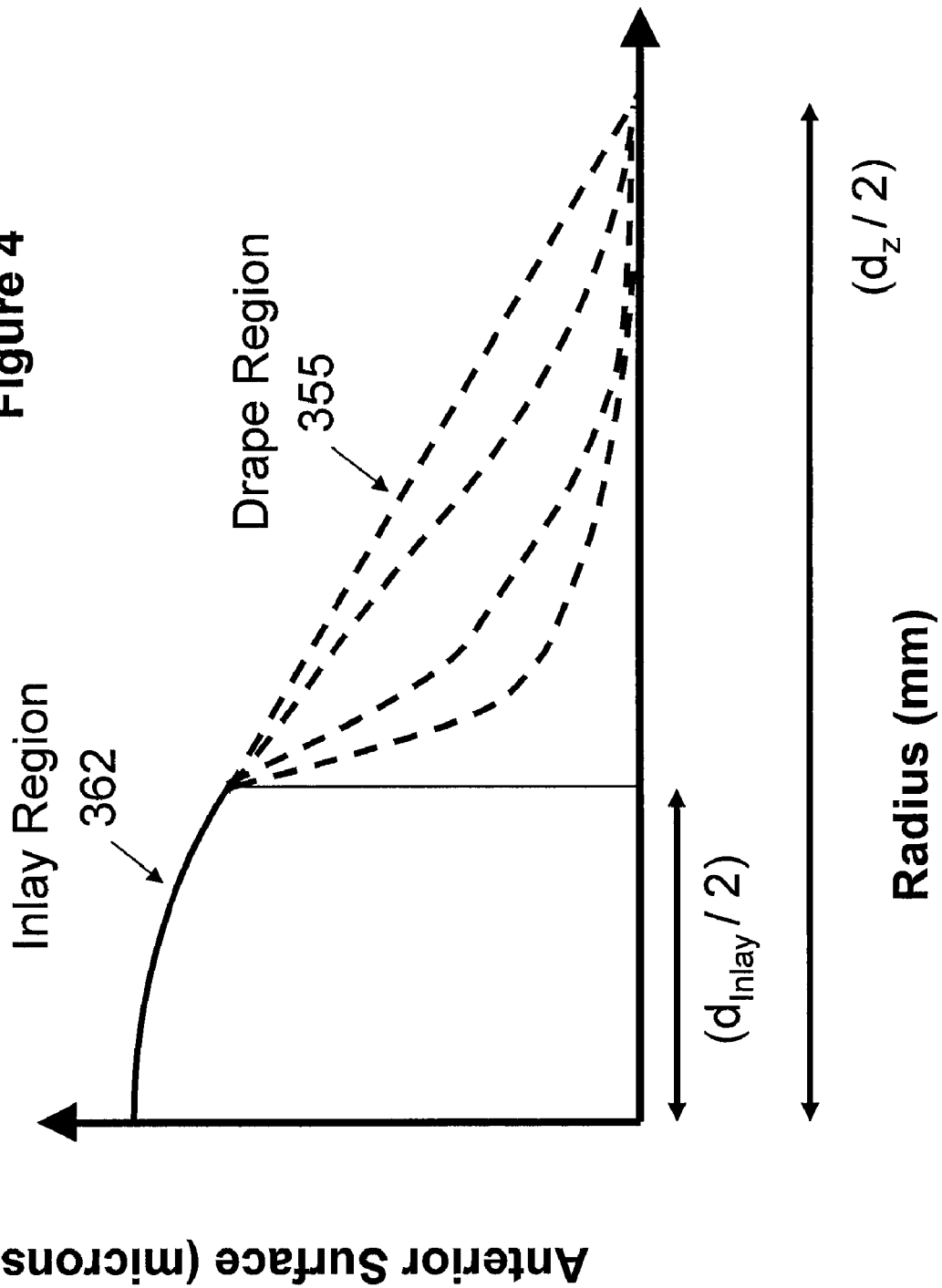
FIG. 4 illustrates various possible shapes for the drape region.

FIG. 4 illustrates a variety of possible draping shapes 355. FIG. 4 shows the radius ($d_I/2$) of an inlay region 362 and the total radius ($d_z/2$) of the shape change due to the draping effect. The possible draping shapes 355 are shown in dashed lines, and may depend on factors such as the edge thickness, the local mechanical properties of the flap material, the diameter of the inlay (dI), the mechanical properties of the inlay material, and other geometric factors. The precise shape of the drape can be approximated by invitro or invivo clinical experiments and/or by complex mechanical modeling using techniques such as finite element analysis.

It is useful to define the optical zone diameter (dz) corresponding to the size of the anterior corneal surface affected by the inlay 210, as shown in FIG. 3. For purposes of the design method, it is sufficient to assume that the relationship between the optical zone and the inlay diameter, given the other variables, can be determined by the methods outlined above.

A method for designing a small inlay to provide near vision according to an embodiment will now be given.

(1) The first step is to determine the maximum optical zone (dz) that is an acceptable tradeoff between the near vision improvement and the loss of distance vision. Considerations include the pupil size of the specific subject or a group of characteristic subjects (e.g., subjects within a particular age range) while reading nearby objects and the pupil size for distance viewing, especially at night. In an exemplary application, the inlay is placed in one eye to provide near vision and distance correction by other means is performed on the fellow eye. In this example, both eyes contribute to distance vision, with the non-inlay eye providing the sharpest distance vision. The eye with the inlay provides near vision.

(2) Given the empirically derived or theoretically derived relationship between the optical zone (dz) and the inlay diameter (dI), approximate the inlay diameter that achieves the optical zone.

(3) Design the inlay using the method outlined in detail below. This methods is similar to the design methods described in U.S. patent application Ser. No. 11/293,644, titled "Design Of Intracorneal Inlays," filed on Dec. 1, 2005, the entirety of which is incorporated herein by reference.

(4) Finally, use optical ray-trace methods to assess the image quality of distance and near images with the inlay using the entire corneal surface (i.e., the corneal surface within the inlay diameter (dI), between the inlay diameter and the optical zone (dz), and the peripheral to the optical zone). Make small adjustments to the inlay design to optimize the distance and near image quality based on the inlay design method outlined below and the predicted drape shape given by the methods described above.

The design method of step three will now be given.

FIGS. 3 and 4 show two regions affected by the inlay design: a "central region" 260 defined by the inlay diameter (dI), and a "drape region" 255 falling between the inlay diameter and the optical zone (dz). The design method described below is used to design inlays to produce desired shapes of the anterior corneal surface in the central region to correct presbyopia. This design method assumes that the inlay material has the same index of refraction as the cornea.

A first step in the design of an inlay in the central region is determining a thickness profile that the inlay must induce on the anterior corneal surface to produce a desired anterior corneal curvature. The desired ADD power needed to provide near focus dictates the desired anterior corneal curvature in the central region (FIG. 4).

A first step in determining the thickness profile of the inlay is to determine an anterior radius of curvature, $r'_a$, that provides the desired refractive change, $\Delta Rx = Rxdist - ADD$, where ADD is the desired ADD power prescribed for near vision and Rxdist is the distance refraction prior to inlay implant. Rxdist is approximately zero diopters for emmetropic individuals, or is equal to the achieved or targeted post-operative distance refraction after a surgical procedure to correct the distance ammetropia. The equivalent change in the cornea's refractive power, $\Delta K_{equiv}$, at the anterior surface is given by:

$$\Delta K_{equiv} = \frac{1}{\frac{1}{Rxdist} - V} - \frac{1}{\frac{1}{ADD} - V} \qquad \text{Equation 1}$$

where V is a spectacle vertex distance, e.g., 0.012 meters, from a spectacle to the cornea's anterior surface. The spectacle vertex distance, V, takes into account that measurements of the cornea's refractive power are typically taken with a spectacle located a distance from the cornea's anterior surface, and translates these power measurements to the equivalent power at cornea's anterior surface.

The pre-implant refractive power at the anterior corneal surface may be approximated by Kavg−Kpost, where Kavg is the average corneal refractive power within approximately the optical zone created by the inlay and Kpost is a posterior corneal refractive power. The desired radius of curvature, $r'_a$, of the anterior surface may be given by:

$$r'_a = \frac{(1.346 - 1)}{(Kavg - Kpost + \Delta K_{equiv})} \qquad \text{Equation 2}$$

For purposes of design and analysis, Kpost may be approximated as −6 diopters. The pre-implant radius of curvature, $r_{preimplant}$, may be approximated by:

$$r_{preimplant} = (1.376 - 1)/(Kavg - Kpost) \qquad \text{Equation 3}$$

The two radius of curvatures need not originate from the same origin.

Figure 5:
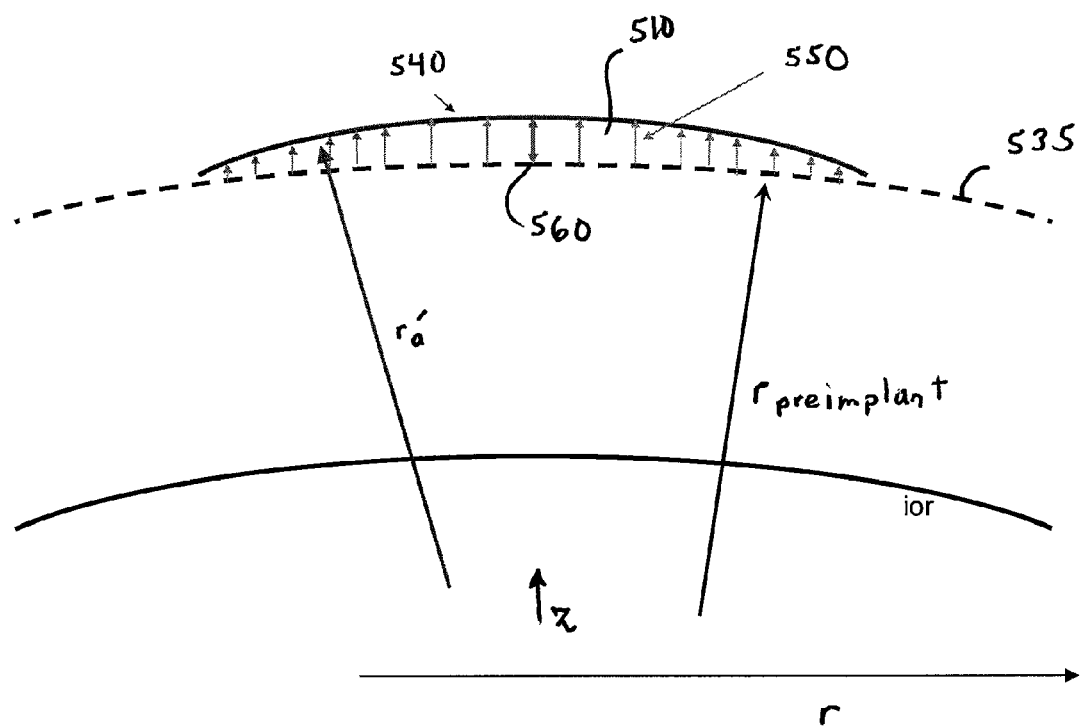
FIG. 5 is a cross-sectional view of a cornea showing a thickness profile for providing a desired refractive correction according to an embodiment of the invention.

FIG. 5 shows a cross-sectional view of a thickness profile 510 specified by a difference between the desired anterior corneal surface 540 and the pre-implant anterior corneal surface 535. In FIG. 5, arrows 550 pointing from the pre-implant anterior surface 535 to the desired anterior surface 540 represent the axial thickness, L(r), of the thickness profile 510 at different positions along an r axis that is substantially perpendicular to an optical z axis. The double arrow 560 represents a center thickness, $L_c$, of the thickness profile. In this embodiment, the thickness profile 510 is rotationally symmetric about the z axis. Thus, the entire thickness profile may be defined by rotating the cross-sectional view shown in FIG. 5 about the z axis.

The thickness L(r) of the thickness profile may be given by:

$$L(r) = L_c + Z_{preimplant}(r; r_{preimplant}) - Z_{anew}(r; r'_a) \text{ and}$$

$$L_c = Z_{anew}(d_I/2) - Z_{preimplant}(d_I/2) \quad \text{Equation 4}$$

where $L_c$ is the center thickness of the thickness profile, $Z_{implant}(r)$ is the pre-operative anterior corneal surface as a function of r, $Z_{anew}(r)$ is the desired anterior corneal surface as a function of r, and $d_I$ is the diameter of the inlay. In the example above, the anterior surfaces $Z_{anew}$ and $Z_{preimplant}$ were assumed to be spherical. This need not be the case. The anterior surfaces may also be aspheric. More generally, the desired anterior surface $Z_{anew}$ may be a function of desired ADD and also more complex design parameters, e.g., an aspheric surface for higher-order aberration correction. Also, the pre-implant anterior surface $Z_{preimplant}$ is generally aspheric. For designs requiring aspheric surfaces, the surface function Z(r) may be given by the general aspheric form:

$$Z(r) = \frac{\frac{r^2}{r_c}}{1 + \sqrt{1 - (1+k)\left(\frac{r}{r_c}\right)^2}} + a_4 r^4 + a_6 r^6 \quad \text{Equation 5}$$

where:
$r_c$ is the radius of curvature
k is a conic constant
$a_4$ and $a_6$ are higher order aspheric constants For a spherical surface, k=0, $a_4$=0, and $a_6$=0. The human cornea may be approximated by k=−0.16, $a_4$=0 and $a_6$=0. The radius of curvature, $r_c$, may be specified by the ADD power for correction of presbyopia, and the other parameters may specify corrections for higher-order aberrations.

The above expressions for the thickness profile are intended to be exemplary only. Other mathematical expressions or parameters may be used to describe similar or other thickness profiles. Therefore, the invention is not limited to particular mathematical expressions or parameters for describing the thickness profile.

After the required thickness profile L(r) is determined, the inlay is dimensioned to have substantially the same thickness profile. The profiles should have the same thickness to within about one micron, which would cause a diopter difference of about one eight of a diopter if the center thickness differs by one micron. An eight of a diopter is half the accuracy with which ophthalmic refractive errors are manually recorded. Next, the thickness profile of the inlay is increased by the finite edge thickness ($h_{edge}$) by the manufacturing process. This finite edge thickness is one factor inducing the drape as illustrated in FIG. 4. When implanted in the cornea, the thickness profile of the inlay is substantially transferred to the anterior corneal surface through the intervening flap, thereby producing the desired post-implant anterior corneal surface in the central region. The draping effect causes the change in the anterior corneal surface thickness to extend beyond the central region. This draping effect can be minimized, e.g., by reducing the finite edge thickness of the inlay as much as possible.

The design method above assumed that the index of refractive of the inlay is the same as the cornea, in which case changes in refractive power of the cornea is due solely to the change in the anterior corneal surface induced by the inlay. An inlay with intrinsic power (e.g., a higher index of refraction than the cornea) may also be used, in which changes in the refractive power is provided by a combination of the physical inlay shape and the intrinsic power (i.e., index of refraction) of the inlay. Design methods for inlays with intrinsic power is described in application Ser. No. 11/381,056, titled "Design Of Inlays With Intrinsic Diopter Power," filed on May 1, the entirety of which is incorporated herein by reference.

Inlays With Increased Effective Optical Zones

For some applications, it is desirable for an inlay to induce an effective optical zone on the anterior corneal surface that is much larger than the inlay diameter. The increase in the effective optical zone allows the inlay to produce a much larger clinical effect on the patient's vision than the actual inlay diameter. In one example, a 1.5 mm-2 mm range diameter inlay has an increased effective optical zone of 4 mm-5 mm, in which the optical effect of the inlay is 2× to 3× greater than its diameter. The increased effective optical zone can also be achieved with inlay diameters outside the above range. For example, the diameter of the inlay may go down to 1 mm or less for some designs, while achieving the desired optical effect.

The increase in the effective optical zone (i.e., "effect" zone) of the inlay can be achieved by increasing the draping effect of the inlay. Increasing the draping effect extends the drape region, and therefore the effective optical zone (i.e., the area of the anterior corneal surface affected by the inlay). The draping effect may be increased, e.g., by increasing the finite edge thickness of the inlay so that the anterior corneal surface returns to its pre-implant surface at a larger radius.

Small diameter inlays inducing effective optical zones much larger than the inlay diameter may be used to correct hyperopia. For example, an inlay with a diameter of 2 mm can provide increased diopter power over an effective optical zone having a diameter of 4 mm. The curvature of the anterior corneal surface in the drape region is greater than the pre-implant anterior corneal surface. Therefore, the draping effect extends the area of the anterior corneal surface where the curvature is increased, thereby extending the effective optical zone of the inlay and providing increased diopter power over a wider diameter than the inlay diameter. This increase in the effective optical zone allows for the correction of hyperopia using smaller diameter inlays.

An inlay with increased effective optical zone may also be used to correct various vision impairments including presbyopia, hyperopia, myopia, and higher order aberrations. In the case of presbyopia, a sufficient "effect" zone may be achieved with an even smaller diameter inlay. For example, a 1 mm diameter inlay may be used to produce a 2 mm diameter "effect" zone.

Figure 6:
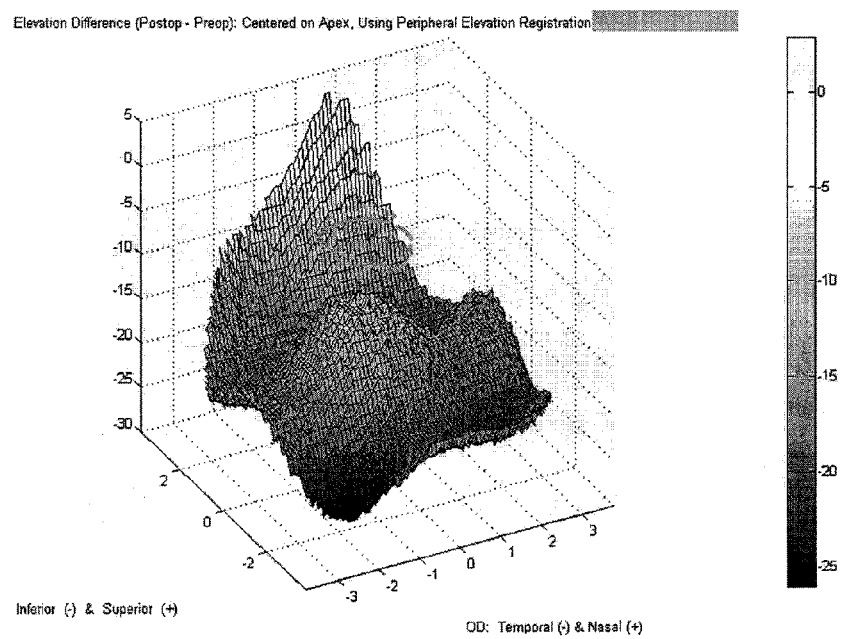
FIG. 6 is a 3D topographic difference map showing the change in the anterior corneal surface induced by an inlay according to an embodiment of the invention.

Clinical data will now be presented in which the effective optical zone induced by an inlay is larger than the inlay diameter. In general, topographic instruments can be used to measure the change in the anterior surface elevation induced by an inlay, calculate the change in the anterior surface curvature and deduce the change in the diopter power. FIG. 6 shows an example of a 3D topographic difference map showing the change in the anterior corneal surface for a subject (subject 1) between a preoperative examination and a one week postoperative examination. In this example, an intracorneal inlay was implanted in subject 1 having a diameter of 2 mm, a center thickness of approximately 36 microns, and an edge thickness of approximately 30 microns. The inlay was placed under a corneal flap created using a laser keratome (by Intralase, Inc.) at a depth of approximately 110 microns. A Scheimpflug topographer ("Pentacam" by Oculus, Inc.) was used to measure the surfaces. From FIG. 6, it is clear that the implanted inlay steepened the anterior corneal surface.

Figure 7:
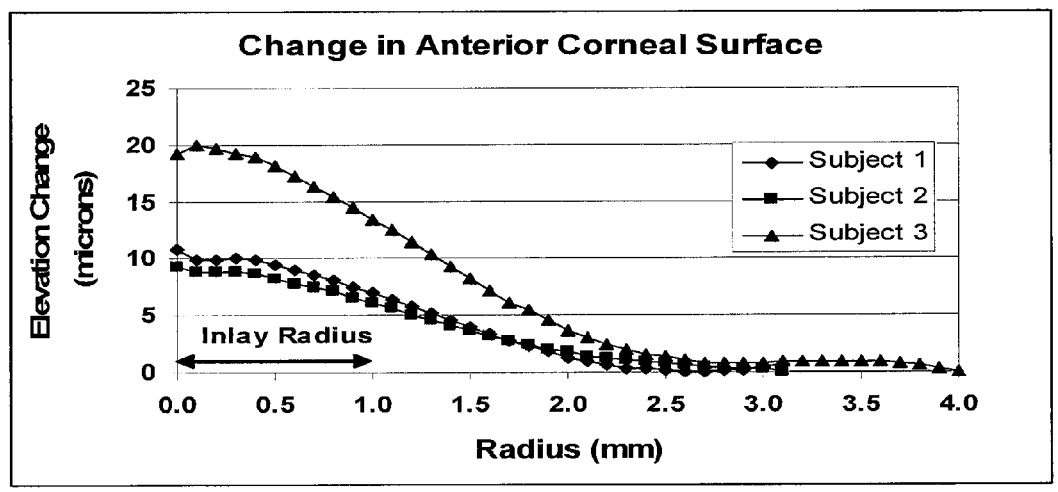
FIG. 7 shows an average radial elevation profile induced by an inlay according to an embodiment of the invention.

FIG. 7 shows the average radial elevation profile calculated from data in FIG. 6. Average radial profiles for two additional subjects (subjects 2 and 3) who received the same inlay design are also shown. Note that the central anterior surface elevation change was less than the center thickness of the inlay. This reflects biomechanical interactions between the inlay material, stromal bed on which it rests and the overlying keratometric flap. However, in all cases the inlay increased the anterior surface elevation beyond the physical diameter of the inlay. FIG. 7 suggests that the effective optical zone induced by the inlay was approximately twice the inlay diameter for this particular design. Inlays with different diameters, center thicknesses and thickness profiles may have different "effect" zone sizes.

Figure 8:
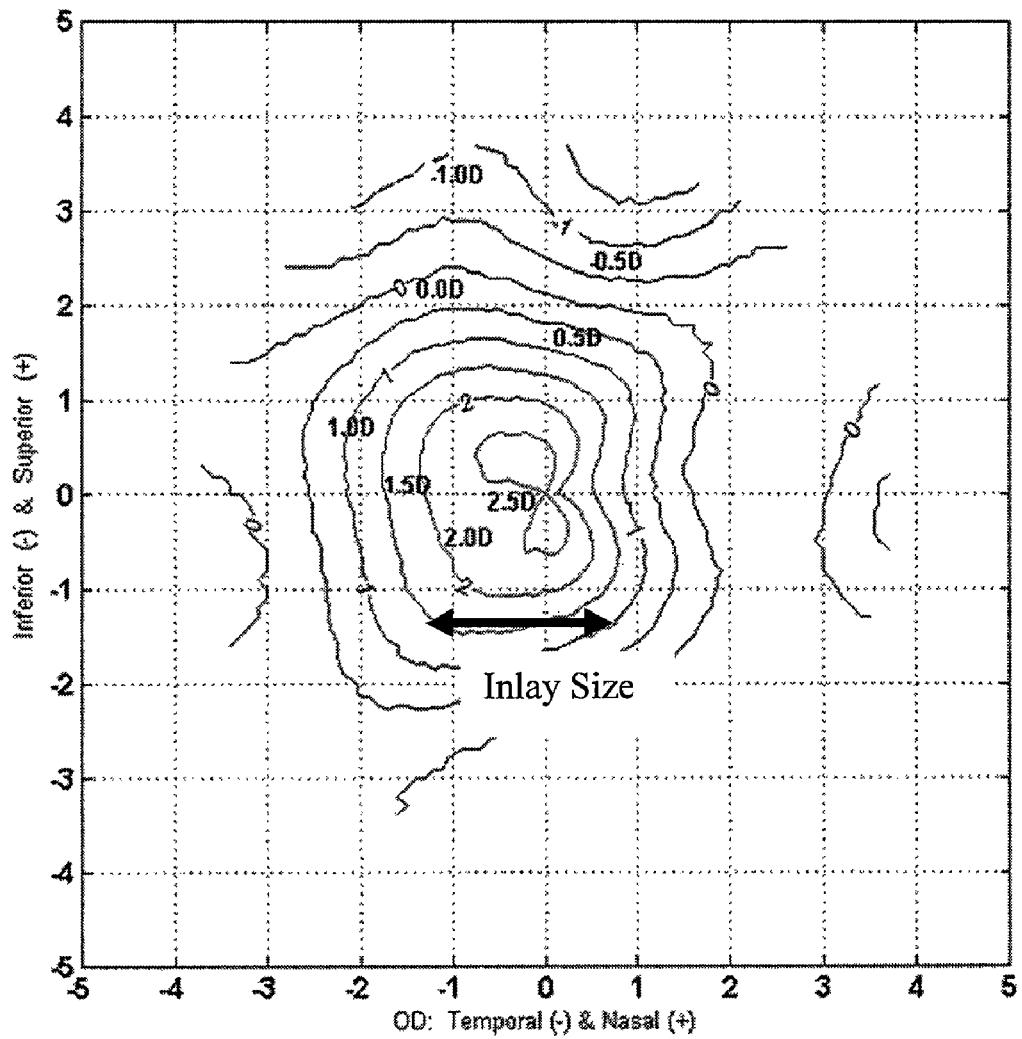
FIG. 8 shows a contour map of the refractive change induced by an inlay according to an embodiment of the invention.

FIG. 8 shows a contour map of the refractive change induced by the intracorneal inlay. This is calculated from the elevation differences by calculating the sagittal curvature map and converting to diopter power using:

$$\text{Diopter power} = (n_c - 1)/\text{sagittal curvature}$$

where $n_c$ is the index of refraction of the cornea. Again, the effective optical zone of the inlay was greater than the diameter of the inlay.

In the foregoing specification, the invention has been described with reference to specific embodiments thereof. It will, however, be evident that various modifications and changes may be made thereto without departing from the broader spirit and scope of the invention. As another example, each feature of one embodiment can be mixed and matched with other features shown in other embodiments. As yet another example, the order of steps of method embodiments may be changed. Features and processes known to those of ordinary skill may similarly be incorporated as desired. Additionally and obviously, features may be added or subtracted as desired. Accordingly, the invention is not to be restricted except in light of the attached claims and their equivalents.

The invention claimed is:

1. A method for treating presbyopia using an intracorneal inlay, comprising:
    altering the shape of the anterior surface of a cornea to correct near vision by implanting the inlay in the cornea, wherein the inlay has a diameter of approximately 2.5 mm or less, and distance vision is provided by a region of the cornea peripheral to an area of the anterior surface affected by the inlay.

2. The method of claim 1, wherein the inlay has an index of refraction substantially equal to the index of refraction of the cornea.

3. The method of claim 1, wherein the inlay has an index of refraction higher than the index of refraction of the cornea.

4. The method of claim 1, wherein the inlay is implanted at a depth of 25% or less of the cornea.

5. The method of claim 1, wherein a curvature of an anterior surface of the inlay is higher than the curvature of the anterior surface of the cornea.

6. The method of claim 1, further comprising:
    prior to implantation of the inlay, performing a corrective procedure on the cornea to correct distance vision.

7. The method of claim 6, wherein the corrective procedure to correct distance vision comprises a LASIK procedure.

8. The method of claim 7, further comprising:
    cutting a flap in the cornea during the LASIK procedure; and
    after the LASIK procedure, reopening the flap and implanting the inlay beneath the flap.

9. The method of claim 1, further comprising performing a corrective procedure to correct distance vision concurrently with implantation of the inlay.

10. The method of claim 9, wherein the corrective procedure to correct distance vision comprises a LASIK procedure.

11. The method of claim 10, further comprising:
    cutting a flap in the cornea during the LASIK procedure; and
    implanting the inlay beneath the flap.

12. The method of claim 1, wherein the inlay has a diameter of approximately 2 mm or less.

13. The method of claim 1, wherein the inlay has a diameter of approximately 1.5 mm or less.

14. The method of claim 1, further comprising:
    cutting a flap in the cornea;
    lifting the flap to expose an interior of the cornea;
    placing the inlay in the interior of the cornea; and
    repositioning the flap over the inlay.

15. The method of claim 1, further comprising:
    cutting a pocket in an interior of the cornea; and
    placing the inlay in the pocket.

16. A method for correcting vision impairment, comprising:
    implanting an inlay having a diameter less than 4 mm in a cornea of an eye, wherein the inlay produces an effective optical zone on the anterior surface of the cornea greater than the diameter of the inlay, wherein the diameter of the inlay is less than the diameter of a dilated or undilated pupil of the eye, and wherein the effective optical zone is smaller than the pupil of the eye.

17. The method of claim 16, wherein the diameter of the effective optical zone is at least 1.5 times greater than the diameter of the inlay.

18. The method of claim 16, wherein the diameter of the effective optical zone is at least two times greater than the diameter of the inlay.

19. The method of claim 16, wherein the inlay increases the curvature of the anterior surface of the cornea, and an area of increased curvature has a diameter greater than the diameter of the inlay.

20. The method of claim 19, wherein the area of increased curvature has a diameter at least 1.5 times greater than the diameter of the inlay.

21. The method of claim 19, wherein the area of increased curvature has a diameter at least 2 times greater than the diameter of the inlay.

22. The method of claim 16, wherein the diameter of the inlay is less than 3 mm.

23. The method of claim 16, wherein the diameter of the inlay is in the range of 1.5 mm to 2 mm.

24. The method of claim 16, wherein the diameter of the inlay is less than 1.5 mm.

25. The method of claim 16, wherein the diameter of the inlay is less than 4 mm and the effective optical zone is 8 mm or less.

26. The method of claim 16, wherein the diameter of the inlay is less than 3 mm and the effective optical zone is in the range of about 6 mm to 8 mm.

27. The method of claim 16, wherein the diameter of the inlay in the range of 1.5 mm to 2 mm and the effective optical zone is in the range of about 4 mm to 5 mm.

28. The method of claim 16, wherein the diameter of the inlay is less than 1.5 mm and the effective optical zone is in the range of about 2 mm to 4 mm.

29. The method of claim 16, wherein the diameter of the inlay is less than 1 mm.

30. The method of claim 16, wherein the diameter of the inlay is less than 1 mm and the effective optical zone is in the range of about 2 mm to 4 mm.

31. The method of claim 16, wherein the center thickness of the inlay is less than 50 μm.

32. The method of claim 16, wherein the inlay is implanted in the cornea at a depth of 170 μm.

33. The method of claim 16, wherein the refractive index of the inlay is in the range of about 1.33 to 1.55.

34. The method of claim 16 wherein the effective optical zone comprises a central region to correct near vision, and wherein distance vision is provided in a region of the cornea peripheral to the effective optical zone.

35. A method for providing near and distance vision in an eye using an intracorneal inlay, comprising:

altering the shape of a region of the anterior surface of a cornea of the eye to provide near vision by implanting an inlay in the cornea, wherein the inlay has a diameter less than 4 mm and less than the diameter of a dilated or undilated pupil of the eye, wherein a region of the anterior surface of the cornea affected by the inlay is larger than the diameter of the inlay; and providing distance vision in a region of the cornea peripheral to the region of the anterior surface of the cornea affected by the inlay.

36. The method of claim 35 wherein the inlay has an index of refraction that is substantially the same as the index of refraction of the cornea.

37. The method of claim 35 wherein the inlay has a diameter less than about 3 mm.

38. The method of claim 35 wherein the inlay has a diameter between about 1.5 mm and about 2 mm.

* * * * *

UNITED STATES PATENT AND TRADEMARK OFFICE

(12)        CERTIFICATE EXTENDING PATENT TERM
UNDER 35 U.S.C. § 156

| | | | |
|---|---|---|---|
| (68) | PATENT NO. | : | 8,057,541 |
| (45) | ISSUED | : | November 15, 2011 |
| (75) | INVENTOR | : | Dishler et al. |
| (73) | PATENT OWNER | : | ReVision Optics, Inc. |
| (95) | PRODUCT | : | Raindrop® Near Vision Inlay |

This is to certify that an application under 35 U.S.C. § 156 has been filed in the United States Patent and Trademark Office, requesting extension of the term of U.S. Patent No. 8,057,541 based upon the regulatory review of the product Raindrop® Near Vision Inlay by the Food and Drug Administration. According to United States Patent and Trademark Office records, the original expiration date of the patent as of the date of issuance of this certificate is January 8, 2029. Because it appears that the requirements of the law have been met, this certificate extends the term of the patent for the period of

(94)                          537 days subject to the payment of maintenance fees as provided by law, with all rights pertaining thereto as provided by 35 U.S.C. § 156.

I have caused the seal of the United States Patent and Trademark Office to be affixed this 3rd day of September 2020.

Andrei Iancu
Under Secretary of Commerce for Intellectual Property and
  Director of the United States Patent and Trademark Office